(12) United States Patent
Merrell

(10) Patent No.: US 9,751,813 B2
(45) Date of Patent: Sep. 5, 2017

(54) SYSTEMS, METHODS, AND APPARATUS FOR CONVERTING BIOSOLIDS TO CLASS A FERTILIZER

(71) Applicant: Merrell Brothers, Inc., Kokomo, IN (US)

(72) Inventor: Ted Merrell, Kokomo, IN (US)

(73) Assignee: Merrell Brothers, Inc., Kokomo, IN (US)

( * ) Notice: Subject to any disclaimer, the term of this patent is extended or adjusted under 35 U.S.C. 154(b) by 0 days.

(21) Appl. No.: 14/729,850

(22) Filed: Jun. 3, 2015

(65) Prior Publication Data

US 2015/0353435 A1 Dec. 10, 2015

Related U.S. Application Data

(60) Provisional application No. 61/997,622, filed on Jun. 6, 2014.

(51) Int. Cl.
*C05F 7/00* (2006.01)
*A61L 2/04* (2006.01)
*A61L 9/014* (2006.01)

(52) U.S. Cl.
CPC ....... *C05F 7/00* (2013.01); *A61L 2/04* (2013.01); *A61L 9/014* (2013.01); *Y02E 50/343* (2013.01); *Y02W 30/47* (2015.05)

(58) Field of Classification Search
CPC ............ A61L 2/04; C05F 7/00; Y02E 50/343; Y02W 30/47
See application file for complete search history.

(56) References Cited

U.S. PATENT DOCUMENTS

| | | |
|---|---|---|
| 4,043,047 A | 8/1977 | Galliker |
| 4,121,539 A | 10/1978 | Moore |
| 4,174,371 A | 11/1979 | Bell et al. |
| 4,249,317 A | 2/1981 | Murdock |
| 4,255,389 A | 3/1981 | Jung et al. |
| 5,361,708 A | 11/1994 | Barnes |
| 5,853,590 A | 12/1998 | Burnham |
| 6,103,191 A | 8/2000 | Luker |
| 6,243,968 B1 | 6/2001 | Conrad et al. |

(Continued)

FOREIGN PATENT DOCUMENTS

| | | |
|---|---|---|
| CN | 2727147 Y | 9/2005 |
| CN | 2752690 Y | 1/2006 |

(Continued)

OTHER PUBLICATIONS

SolorOrganite. <https://web.archiye.org/save/_embed/https://sites.google.com/site/solarorganite/home> pp. 1-18 (May 27, 2013).*

(Continued)

*Primary Examiner* — Jennifer A Smith

(57) ABSTRACT

A system and methods comprising a greenhouse for predrying a biosolids to reduce volume and weight; a conveyer belt operably connected to the greenhouse for conveying the biosolids from the greenhouse to a pasteurization system; the pasteurization system comprising a burner-fan to introduce hot air to the biosolids; the pasteurization system comprising a heat up belt to accept the biosolids from the greenhouse and a burner-fan for raising the biosolids temperature from ambient to at least 70° C.; the pasteurization system further comprising a pasteurization belt to hold the biosolids at 70° C. for at least thirty minutes; a biofilter system operably connected with the greenhouse and the pasteurization system for reducing odors; and bagging area to collect a final product.

17 Claims, 3 Drawing Sheets

(56) References Cited

U.S. PATENT DOCUMENTS

| | | | |
|---|---|---|---|
| 7,240,440 | B2 | 7/2007 | Delons |
| 7,434,332 | B2 | 10/2008 | Morton et al. |
| 8,124,401 | B2 | 2/2012 | Dutil et al. |
| 8,468,714 | B2 | 6/2013 | Conrad et al. |
| 8,926,791 | B2 | 1/2015 | Hammond |
| 2005/0028680 | A1* | 2/2005 | Thompson ............ C02F 11/185 99/455 |
| 2011/0159576 | A1 | 6/2011 | Arnold |
| 2012/0074057 | A1 | 3/2012 | Kovalak |
| 2013/0146533 | A1* | 6/2013 | Arnoldsen, Jr. ........ C02F 3/284 210/603 |
| 2013/0333236 | A1 | 12/2013 | Grosser |
| 2015/0353435 | A1* | 12/2015 | Merrell ...................... C05F 7/00 71/12 |
| 2015/0354893 | A1* | 12/2015 | Hammond ............. F26B 3/286 34/512 |

FOREIGN PATENT DOCUMENTS

| | | |
|---|---|---|
| CN | 201217645 Y | 4/2009 |
| CN | 201809266 U | 4/2011 |
| CN | 102643007 A | 8/2012 |
| CN | 102765864 A | 11/2012 |
| CN | 202610086 U | 12/2012 |
| CN | 202829795 U | 3/2013 |
| CN | 103359904 A | 10/2013 |
| CN | 104014580 A | 9/2014 |
| DE | 20304220 U1 | 5/2003 |
| DE | 202006008137 U1 | 11/2006 |
| DE | 102011018279 A1 | 10/2012 |
| EP | 2013148 B1 | 12/2011 |
| EP | 1644679 B1 | 4/2012 |
| EP | 1464628 B1 | 10/2012 |
| FR | 2927693 A1 | 8/2009 |
| KR | 20110100688 A | 9/2011 |
| RU | 2111938 C1 | 5/1998 |
| WO | 2004020922 A1 | 3/2004 |

OTHER PUBLICATIONS

Alderman, Douglas J. "Class A Continuous-Flow Microwave System."Proceedings of the Water Environment Federation 2004.1 (2004): 730-736.*

Force, Jim. "Sun-Dried Success. Treatment Plant Operator" (Nov. 2011).*

USEPA, EPA. "8342-F-00-067,(Sep. 2000) Biosolids and Residuals Management Fact Sheet." Odor Control in Biosolids Management.*

Bennamoun, L., "Solar drying of wastewater sludge: A review," Renewable and Sustainable Energy Reviews; 2012; pp. 1061-1073; vol. 16; Elsevier Ltd., Algeria (13 pages).

Slim, R., et. al., "Modeling of a solar and heat pump sludge drying system," International Journal of Refrigeration; 2008; pp. 1156-1168; vol. 31, Elsevier Ltd. and IIR; France (13 pages).

Salihoglu et al., "Solar drying in sludge management in Turkey," Renewable Energy; 2007; pp. 1661-1675; vol. 32; Elsevier Ltd., Turkey (14 pages).

Romdhana, M. H. et al., "Monitoring of pathogenic microorganisms contamination during heat drying process of sewage sludge," Process Safety and Environmental Protection; 2009; pp. 377-386; vol. 87; Elsevier B.V.; France (10 pages).

Seginer, I. et al., "Modeling Solar Drying Rate of Wastewater Sludge," Drying Technology: An International Journal; 2006; pp. 1353-1363; vol. 24; Taylor & Francis Group, LLC; Israel (12 pages).

Mathioudakis, V.L. et al., "Extended Dewatering of Sewage Sludge in Solar Drying Plants," Desalination; 2009; pp. 733-739; vol. 248; Elsevier B.V., Greece (7 pages).

Luboschik, U., "Solar Sludge Drying—Based on the IST Process," Renewable Energy; 1999; pp. 785-788; vol. 16; Elsevier Science Ltd.; Germany (14 pages).

Seginer, I. et al., "Optimal Control of Solar Sludge Dryers," Drying Technology 2007; pp. 401-415; vol. 25; Taylor & Francis Group, LLC; Israel (16 pages).

Bux, M. et al., "Class-A by Solar Drying Recent Experiences in Europe," Proceedings of the Water Environment Federation, WEFTEC 2001: Sessions 41-50; pp. 309-317; Germany (9 pages).

Lei, Z. et al., "Seware Sludge Solar Drying Practise and Characteristics Study," Asia-Pacific Power and Energy Engineering Conference; 2009; pp. 1-5; IEE Explore; China (5 pages).

Zwiefelhofer, Hans P., "Aerobic-thermophilic/anaerobic-mesophilic two-stage sewage sludge treatment: Practical experiences in Switzerland," Conservation & Recycling; 1985; pp. 285-301; vol. 8, No. 1/2; Pergamon Press Ltd.; Great Britain (17 pages).

Hudson, J.A. et al., "Current Technologies for Sludge Treatment and Disposal," Water and Environmental Journal; Dec. 1996; pp. 436-441; vol. 10; Wiley; United Kingdom (6 pages).

* cited by examiner

SYSTEMS, METHODS, AND APPARATUS FOR CONVERTING BIOSOLIDS TO CLASS A FERTILIZER

This application claims priority to U.S. provisional patent application Ser. No. 61/997,622 filed Jun. 6, 2014.

BACKGROUND OF THE INVENTION

Biosolids are the solid, semi-solid, or liquid residue generated during the biological wastewater treatment process. Biosolids for beneficial use (i.e. land application, marketing or distribution) must be treated to reduce pathogens and vector attraction ("VAR").

Insects, birds, rodents, and domestic animals may transport sewage sludge and pathogens from sewage sludge to humans. Vectors are attracted to sewage sludge as a food source, and the reduction of the attraction of vectors to sewage sludge to prevent the spread of pathogens is a focus of federal regulation. VAR can be accomplished in two ways: by treating the sewage sludge to the point at which vectors will no longer be attracted to the sewage sludge or by placing a barrier between the sewage sludge and vectors.

After the treatment of wastewater is performed, the generated biosolids needs to be beneficially reused or disposed. Generally, biosolids are hauled from wastewater treatment plants and beneficially reused in rural farm areas where biosolids are applied to farm fields or are transported to a landfill for disposal. Large volumes of sludge (biosolids) create large transportation expenses. Wastewater sludge contains relatively high percentage of water, and large volumes are created for transport out for reuse or disposal. The sludge also can create environmental and or health problems.

Federal, state and local governments regulate the distribution and marketing of Class A biosolids. Class A biosolids represent the highest quality biosolids produced and may be used as fertilizer through commercial distribution and marketing. To achieve a Class A status, the biosolids must be treated to a level that essentially nearly eliminates pathogens and must meet stringent maximum concentration limits for heavy metals. Class A biosolids may be distributed in bulk or bagged for sale at retail centers. Class A biosolids may be marketed in different physical forms, and, like traditional commercial fertilizer, are not subject to site management restrictions if the product is registered as a fertilizer or distributed and marketed to a person or entity that will sell or give-away the biosolids (wholesale) or market biosolids products as a fertilizer (retail).

The United States Environmental Protection Agency's (EPA) Regulations recognize at least two classes. Class B pathogen reduction standards, as set forth in 40 C.F.R. 503, require a fecal coliform level of less than two million most-probable-numbers (MPN) per gram of total solids. Class A pathogen standards, (40 C.F.R. 503) require fecal coliform densities are less than 1,000 MPN per gram total solids; or when *Salmonella* densities are less than 3 MPN per four grams total solids. Additionally, enteric virus must be less than 1 plaque-forming unit per four grams of total solids, and helminthes ova must be less than one viable helminthes ova per four grams of total solids.

Traditionally, biosolids disposal involves trucking the sludge to rural areas and applying the sludge onto fields. This process increases health and environmental concerns. Other methods of disposal may include incineration, adding chemicals, or disposal into landfills. Concerns about contaminants, runoff, air pollution, tipping fees, and rising transportation costs have resulted in cities and municipalities seeking alternate, more efficient methods to handle the removal of biosolids.

SUMMARY OF THE INVENTION

This invention involves generally a system and method for greenhouse pre-drying of the biosolids followed by controlled pasteurization to derive a Class A fertilizer product. In one preferred embodiment, a greenhouse contains the biosolids to pre-dry it to a desired level. The desired pre-drying level is within the range of about 60 to about 70% solids (30-40% moisture) by weight. After pre-drying, the biosolids enter a fueled pasteurization system. The function of the pasteurization system is twofold. First, it raises the temperature of the biosolids from ambient temperature to a minimum of 70° C. Second, it decreases the moisture content (increase the solids content) of the biosolids to meet or exceed 75% solids. Once the biosolids reaches 70° C. or higher, the belt pasteurization chamber maintains the biosolids at that temperature for at least thirty (30) minutes. The pasteurization system then discharges the biosolids to a container. The finished product meets the highest level of treatment requirements of Class A as defined by the EPA Regulations Part 503 Process to Further Reduce Pathogens ("PFRP") for Pasteurization of the biosolids to destroy pathogens and by increasing the solids content above 75% to achieve the required VAR to meet the requirements for Class A biosolids. The resulting fertilizer product can be reused in bulk or bagged for retail marketing.

This summary is not intended to identify key or essential features of the claimed subject matter, nor is it intended to be used as an aid in limiting the scope of the claimed subject matter. Further embodiments, forms, objects, features, advantages, aspects, and benefits shall become apparent from the following description and drawings.

DESCRIPTION OF ILLUSTRATIVE EMBODIMENTS

Figure 1:
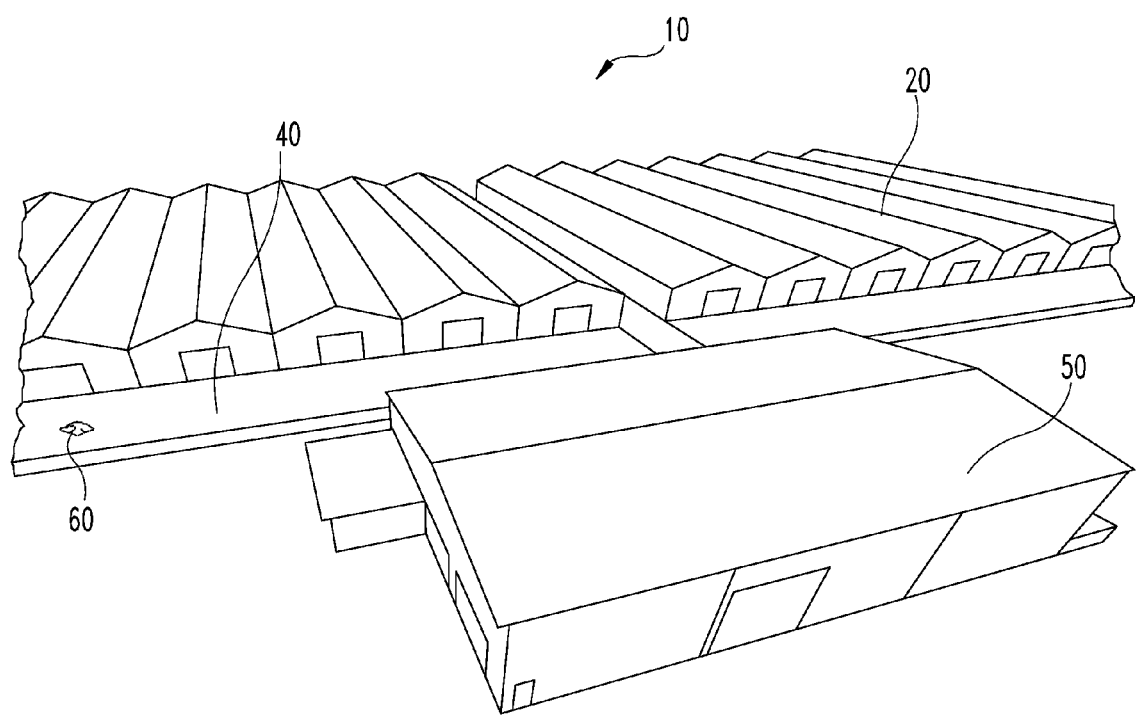
FIG. 1 shows a perspective view of the greenhouses and the pasteurization building.

The following detailed description provides contemplated modes of carrying out embodiments of the invention. The description is not to be taken in a limited sense but to be made for the purpose of illustrating the general principle of the invention since the scope of the invention is best defined as seen below. For the purposes of promoting an understanding of the principles of the invention, reference is made to the embodiments illustrated in the drawings and specific language describes the same. No limitation of the scope of the invention is intended. Alterations, modifications and differing applications as illustrated therein as would occur to one skilled in the art to which the invention relates are contemplated.

Referring to FIG. 1, a greenhouse 20 holds the biosolids 30 (FIG. 2) upon arrival at the treatment complex 10. A biofilter system 40 operates with the greenhouse 20 to reduce odors. A pasteurization building 50 contains the operative pasteurization equipment. Odor control can be handled using media bed 60 such as a woody mulch material designed into a biofilter system 40. The biofilter system 40 may include a forced air duct distribution system 75 (shown in FIG. 3) that discharges the air into an air plume underneath a bed of woody media material. The carbon in the media bed 60 creates an environment for microbes to thrive and thus there is a degradation of the absorbed odorous compounds to renew the absorptive capacity of the media. The media bed 60 may be open to the environment, covered, or enclosed for a stack discharge Other odor control systems such as Packed-tower wet scrubbers, Fine-mist Wet Scrubbers, Activated Carbon Absorbers and Thermal Oxidizers may also be used. The basis for Packed-Tower Wet Scrubbers is the induction of intimate contact between the contaminant odorous air and a scrubbing solution, causing a mass transfer between the two media in which contaminant molecules are absorbed into the liquid. Fine-mist Wet Scrubbers treat odor by bringing the air in contact with 10 micron-sized droplets of scrubber solution generally produced through atomizers using compressed air. Activated Carbon Absorbers possesses a high surface area per unit weight, an intricate pore structure and a primarily hydrophobic surface. Thermal Oxidation Systems oxidize organic compounds into carbon dioxide and water vapor.

Figure 2:
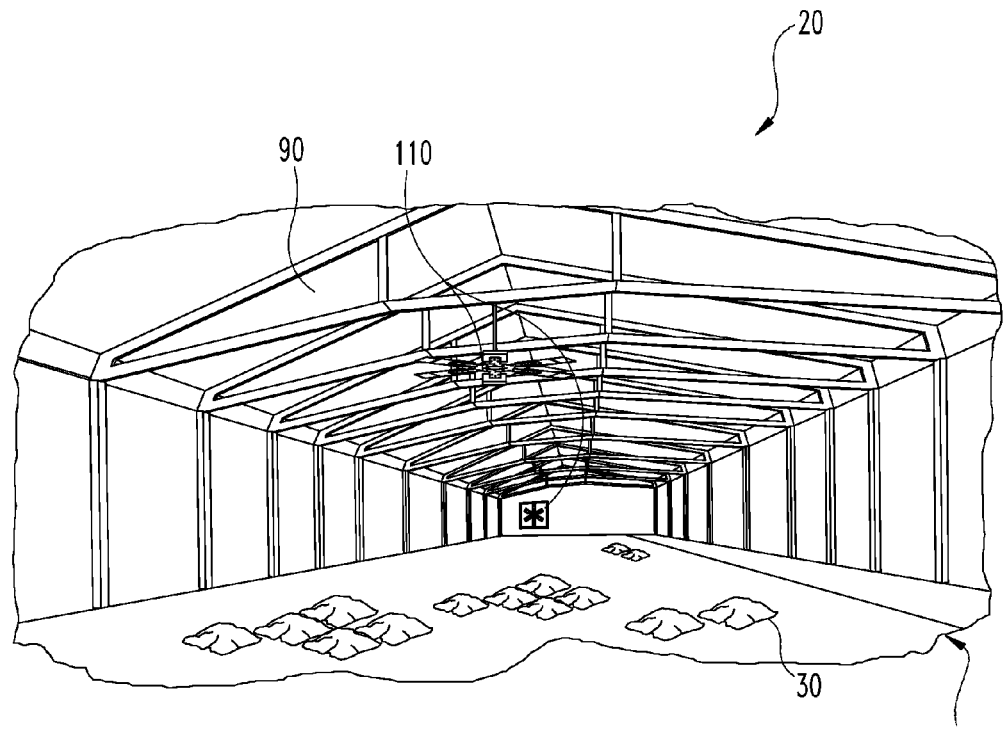
FIG. 2 shows an interior view of the biosolids within the greenhouses.

Referring to FIG. 2, the biosolids 30 is distributed within the greenhouse 20 to pre-dry the biosolids 30 to a desired level. The desired level of pre-drying is between 60 to 70% solids (30 to 40% moisture) by weight. Pre-drying to levels below or above this target range can still be operable but will require additional handling to avoid biosolids 30 that are too wet or too dry for the treatment complex 10. This pre-drying reduces the volume of material that enters the pasteurization building 50 to increase the efficiency of the pasteurization process. Circulation fans 110 may be positioned throughout the greenhouse 20.

The greenhouse 20 allows for the biosolids 30 to be placed on the floor 80 to maximize the surface area of exposure to sunlight through a clear cover 90. Glass, polycarbonate or other suitable materials such as Lexan suffice for the clear cover 90.

Figure 3:
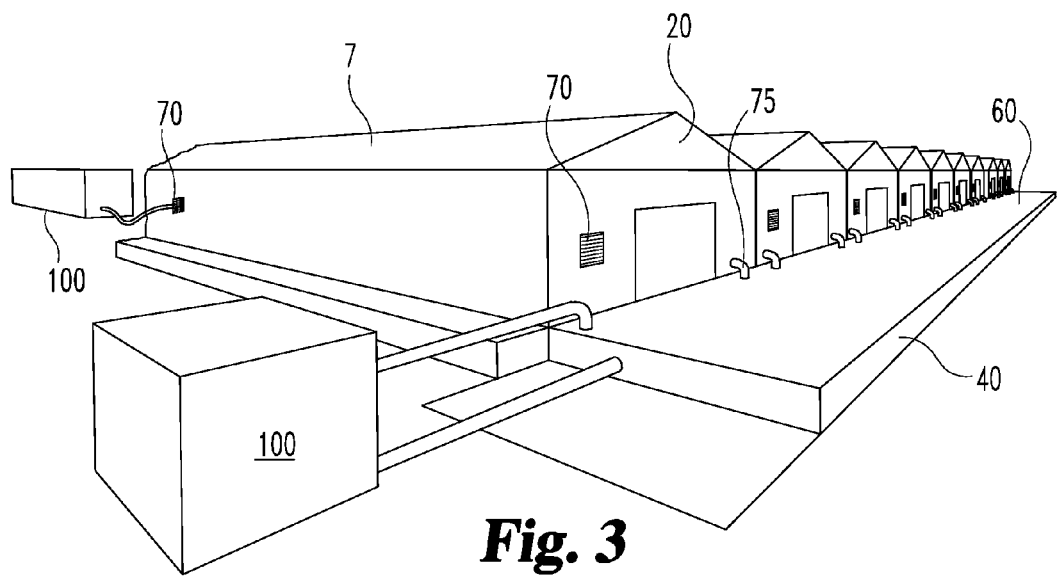
FIG. 3 shows an exterior view of the greenhouse with air inlets for ventilation control and an odor control biofilter system.

FIG. 3 shows a perspective view of the greenhouse 20 having vents 70 for controlling airflow and temperature within the greenhouse 20. The greenhouse 20 can also be equipped with air handlers/exchangers 100 to maximize the vaporization of water from the biosolids 30. The air handlers 100 may be operably connected with the biofilter system 40. The air handlers 100 may be local or remote. These ventilation controls 70 may be manual or may be automated to achieve the desired number of air exchanges within the greenhouse 20. Selective control of the ventilation controls 70 impacts the drying rate of the biosolids 30 by removing the high moisture air out through an exhaust fan 75 to the biofilter system 40 and introducing fresher, lower humidity air that may absorb additional moisture from the biosolids 30. In one embodiment air enters vents 70 and exits at exhaust fans 75 the other end of the greenhouse 20.

Air circulation within the greenhouses can be also accomplished with circulation fans 110 that keep the hot moist air moving throughout the greenhouse 20 until such time as it is exchanged using the exhaust fans 75 and the biofilter system 40. The air handlers 100 can also circulate air to and from the biofilter system 40. Alternatively, the air handlers 100 may either work as heat exchangers or coolers depending on the desired effect. The air circulation may be manual or automated depending on the humidity levels contained within the greenhouse 20. Generally, the greater the air circulation the greater the pre-drying performance. The air can be transferred through exhaust fans 75 into a biofilter system 40 to remove odorous emissions.

The biosolids 30 can be mechanically turned at select time intervals to allow moist biosolids 30 to be exposed to air and the solar sunlight for the drying process. The pre-drying process continues until the biosolids 30 reach a desired dryness, e.g. 60 to 70% solids (30 to 40% moisture) by weight. With increased air handling and management, this range could be widened to 50 to 80% solids (20 to 50% moisture).

Figure 4:
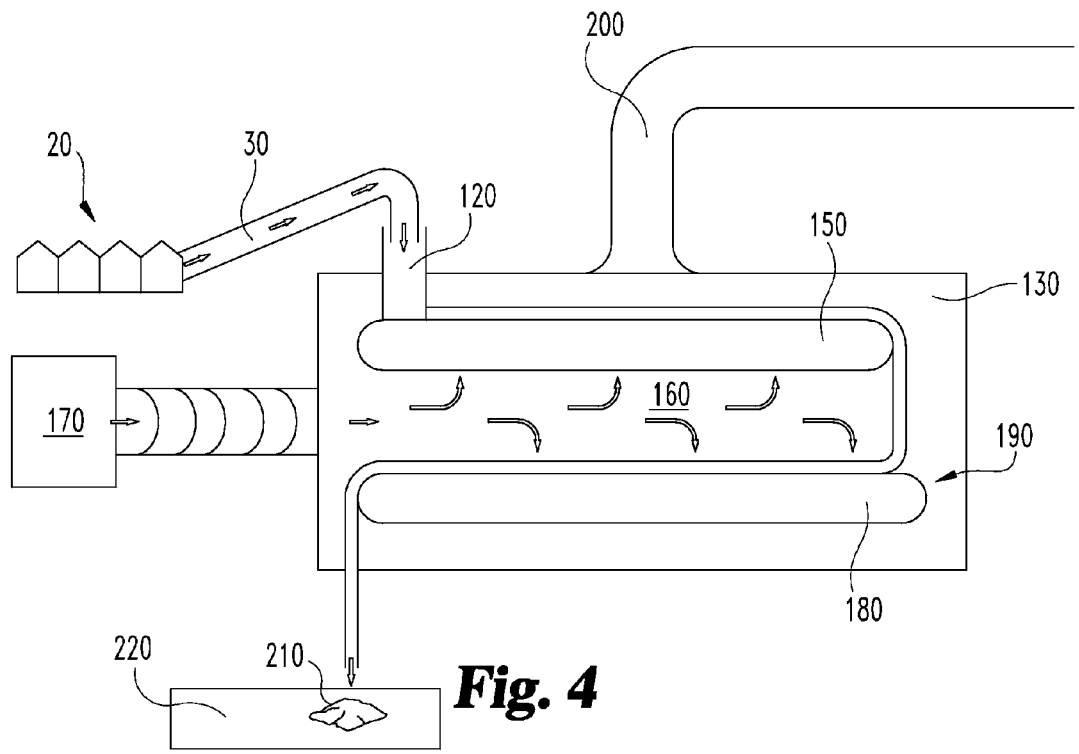
FIG. 4 shows a cross-section of the pasteurization system.
Figure 5:
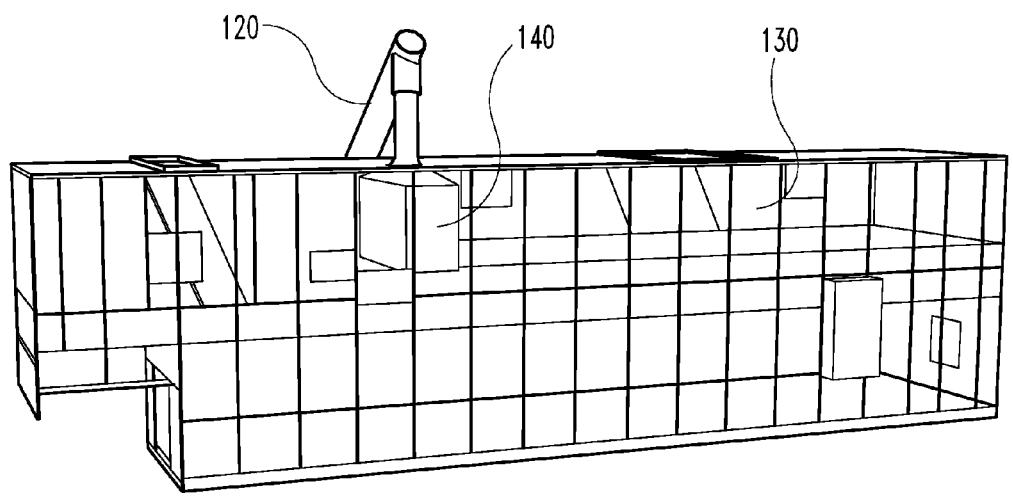
FIG. 5 shows a cross-section of an embodiment with a storage hopper.

Referring to FIG. 4, after pre-drying, the biosolids 30 are conveyed into the pasteurization building 50. An inlet 120, accepts biosolids 30 from the greenhouse 20. The biosolids 30 are conveyed without crushing or pulverizing the biosolids 30. The biosolids 30 can be fed into a pasteurization system 130 or the biosolids 30 can be transferred into a day storage hopper 140 (FIG. 5) before being fed to the pasteurization system 130.

The pasteurization building 50 houses the pasteurization system 130. The pasteurization system 130 includes at least two woven belts that are porous to allow hot air or gas to pass through the belts and thus through the biosolids that is traveling on the belts. The heat up belt 150 raises the temperature of the biosolids 30 from ambient temperature to at least 70° C. The heat up belt 150 receives the biosolids 30 at a controlled even depth. The heat up belt 150 carries the biosolids 30 as the hot air or hot gas 160 passes through the porous belt and the biosolids 30. The hot air or hot gas 160 raises the temperature of the biosolids 30 from ambient temperature to a minimum of 70° C. as the biosolids 30 travels across the heat up belt 150. The speed of the heat up belt 150 can be manually or automatically controlled to assure that the desired end temperature of the biosolids 30 is achieved by the time the biosolids 30 finishes its journey through on the heat up belt 150. During this heat up process, the biosolids 30 loses moisture, dries, and achieves the desired rise in the solids content to achieve the VAR requirement goal of a minimum of 75% solids. The heat up belt 150 may have a variable speed control to ensure the biosolids remain at the desired temperature for the desired time.

A burner and fan 170 provide heat (hot air or hot gas) to the pasteurization system 130 and heat up belt 150 to raise the temperature of the biosolids 30 to a desired temperature. The burner and fan 170 may comprise any type of heat exchanger capable of producing the BTU's necessary to achieve the desired temperature of the hot air or hot gas 160. The burner 170 can be fueled with natural gas, liquid petroleum, digester gas, landfill gas, methane gas electricity or any other fuel source capable of producing the necessary BTU's.

Once the desired temperature has been reached on the heat up belt 150, the biosolids 30 transfer to the pasteurization belt 180. The pasteurization belt 180 conveys the biosolids through the pasteurization chamber 190 for a minimum of 30 minutes at a temperature of at least 70° C. The pasteurization belt 180 is woven porous material to allow hot air or hot gas 160 to pass through the belt 180 and thus pass through the biosolids 30.

The hot air or hot gas 160 passes through the heat up belt 150, the pasteurization belt 180, and biosolids 30 by being drawn through the belts and the biosolids by an exhaust blower 200. The exhaust blower 200 can either be open vented or it can be cyclone vented to allow for the capture of fine dust particles. The exhaust air may also be passed through a biofilter system 40 to capture odors that may be produced in the pasteurization process. The hot air or hot gas 160 passing through the pasteurization chamber 190 may be manually controlled or it may be automated to achieve the desired goal of maintaining at least 30 minutes of at least 70° C. The final product 210 can then be shipped in bulk or be bagged for beneficial reuse.

Greenhouse drying is used throughout the United States and the world to further dry biosolids and to reduce volumes. Reducing the total volume of product helps to reduce the transportation costs. Greenhouse drying alone does not allow for biosolids to achieve high enough temperatures to achieve Class A or AA standards as defined by the EPA regulations for pasteurization. Adding the pasteurization process using a natural, LP or other forms of fuel or electricity completes the desired results of producing an economical pasteurized final product 210 that can have a beneficial use.

The present invention adds more rapid drying of wastewater sludge (biosolids) 30 and provides heat and proper levels of temperatures that exceed US EPA Pasteurization requirements. The pasteurization chamber 190 works well with high volume biosolids 30. The resulting, pasteurized biosolids 210 are then discharged from the chamber 190 into the fertilizer holding/bagging area 220.

In one embodiment, there are two "pods" of greenhouses 20 measuring 294 feet wide by 214 feet long. Each pod consists of seven greenhouses 20 that are connected side by side and open throughout the connecting (214 feet long) sides. Each greenhouse 20 unit is 42 feet wide by 214 feet long. At the end of each greenhouse 30, a 20 feet runway/turning area for equipment exists resulting in 40 feet of each greenhouse section being unavailable for drying. The usable area of each greenhouse 20 is 174 feet long by 42 feet wide or 7,308 square feet.

As an example, one may assume 50,000 wet tons per year throughput. The dewatered biosolids 30 weighs 1,620 lbs. per cubic yard. Trucks deliver biosolids 30 six (6) days per week. In the greenhouse 20, the biosolids 30 may be spread an initial depth of 6 inches. The depth of the biosolids 30 may vary but will affect the rate of drying. Based on the above assumptions of 50,000 wet tons per year multiplied by 2,000 lbs. per ton, 100,000,000 lbs. of biosolids may be introduced each year. That equates to 1,923,076 lbs. per week divided by 1,620 lbs. per cubic yard equals or 1,187 cubic yards per week incoming. 1,187 cubic yards per week divided by 6 days per week equals 197 cubic yards per day incoming.

Using the available square feet capacity of each greenhouse 20 (7,308 multiplied by a 6 inch initial placement depth), 3,654 cubic feet divided by 27 cubic feet per cubic yard equates to 135 cubic yards of capacity per greenhouse 20. Dividing the calculated incoming volume of 197 cubic yards by the single greenhouse 20 capacity of 135 cubic yards, 1.45 greenhouses 20 per day will be required to handle in the design flow. Since there are 14 greenhouses 20 if you divide 14 by 1.45 greenhouses needed per day, it equals 9.6 days of capacity plus one day per week of no incoming biosolids leaving an effective cycle capacity of 10.6 days.

As a further example, one may assume the volume of the biosolids 30 will shrink by 65% as a result of the greenhouse 20 drying. Biosolids will dry from an average incoming 16% solid to an outgoing (pre-pasteurization) solid content of 65%. Using the incoming volume of 197 cubic yards per day, multiplied by a shrinkage factor of 65%, 68.95 cubic yards of product will be removed from the greenhouses 20 per day, 6 days per week. The bulk density of a cubic yard of biosolids 30 is the same for incoming and outgoing product of the greenhouse 20. This would be 1,620 lbs. per cubic yard. Incoming biosolids 30 to the greenhouses 20 average percent solids of 16% solids. Outgoing biosolids from the greenhouses 20 of 65% solids.

As an example, using 100,000,000 lbs. of incoming biosolids 30, the treatment complex 10 and method anticipates a 65% shrinkage by volume. The 65% shrinkage by volume equates to 65% shrinkage by weight resulting in 65,000,000 lbs. of water evaporated and removed from the greenhouses 20. In turn, 65,000,000 lbs. divided by 365 days a year results in an average of 178,082 lbs. of water removed from the biosolids 30 each day. This moist air would be removed by the fan system 75 into the biofilter system 40 where most of the water would be absorbed into the media bed 60 and evaporated out of the media bed 60 while any vapor that would transition back to water would be collected via the internal perimeter drainage system of the biofilter system 40.

With respect to the pasteurization system processing capacity, the chamber 130 has a heat up belt 150 capacity of 24 feet long by 8 feet wide. This belt 150 brings biosolids 30 up to temperature and then delivers the biosolids 30 to the pasteurization belt 180, which has a capacity of 24 feet long by 8 feet wide. The ramp up belt 150 allows for product depth of 3 inches. The pasteurization belt 180 provides for a product depth of 12 inches (biosolids 30 already at a uniform temperature at this point). It takes about eight (8) minutes to raise the average temperature of biosolids 30 from ambient temperature to 170° F.

The heat up belt 150 is variable speed controlled. In one embodiment, the heat up belt 150 is set on a 10 minute cycle speed from the time biosolids 30 hit the belt 150 until biosolids 30 reach the far end of the heat up belt 150 loop. The speed may be varied depending on the amount of water in the biosolids 30. The volume of biosolids 30 on the heat up belt 150 cycles about every 10 minutes. Therefore, based on the capacity of the heat up belt 150 (24 feet long multiplied by 8 feet wide multiplied by a 3 inch product depth), about 48 cubic feet of biosolids 30 reach 170° F. every 10 minutes. Using 27 cubic feet per cubic yard, this equates to 1.77 cubic yards of biosolids 30 being cycled every 10 minutes.

The pasteurization belt 180 can be set on at least a 30 minute cycle time and can be kept at a minimum temperature zone of at least 160° F. to meet acceptable pasteurization standards of 30 minutes at 70° C. (158° F.). The cycle time may vary depending on climate conditions.

Based on the daily production of 68.95 cubic yards, divided by the processing capacity of 1.77 cubic yards every 10 minutes, the treatment complex 10 permits about 38.95 "10 minute" intervals or 389.5 minutes of processing per day. 389.5 plus an additional 40 minutes of oven and personnel startup and 40 minutes of shut down time, equates to 469.5 minutes, divided by 60 minutes an hour, equals 7.82 hours per day of total processing time.

Each of the greenhouse 20 pods has about 754,992 interior cubic feet. There are seven gable roofs with a 4:12 pitch per greenhouse pod 20. The gable area adds an additional 220,206 cubic feet of volume for a total of 975,198 cubic feet of interior air space in each pod. In one embodiment, four exhaust fans 75 associated with each of the seven greenhouses 20 results in 28 fans for each pod (56 total). These fans are rated at 7,300 cfm resulting in 204,400 cfm of air being exchanged. This calculates out to Ser. No. 12/264,000 cubic feet per hour. By dividing 12,264,000 by the total volume of air in the building of 975,198, it results in 12.57 air exchanges per hour. This exchange rate meets the suggested National Fire Protection Association's (NFPA) standards to reduce the possibility of accumulation of combustible vapors for continuously vented areas having exposed biosolids.

One of the key aspects of encouraging the water in biosolids 30 to vaporize into the air is to increase the air flow at the surface of the solids. This encouragement is accomplished in three primary ways. First of all, one cane mix the biosolids 30 with the conventional mixing equipment to blend and mix the dryer surface layer of the biosolids with the moist material underneath the surface. Thus, exposing more moist product to the surface. Second, the exhaust fans 75 create air movement by exchanging the entire volume of air inside the greenhouses 12.57 times an hour. Third, one may include ceiling mounted air circulation fans 110 inside the greenhouses to create excessive air movement which will not only aide in the drying process but it will also circulate the air zones to reduce moisture accumulation on the galvanized steel and its Lexan coverings. This excessive air movement would be accomplished by using six large fans 110 in each pod (12 total) that are rated to move 378,804 cfm. These fans move a total of 2,272,824 cfm per pod. This amount of air movement will rotate and displace the entire air volume in each pod of greenhouses 20 every 26 seconds. This air activity encourages the transition of water into vapor thus accelerating the drying process.

The biofilter system 40 is critical for proper reduction of odors. In one embodiment, a wood-chip/organic-mulch blend 60 is used and allows for maximum porosity while still maintaining acceptable humus to support microbial population. The porosity is important to reduce the potential for pressure drop throughout the life of the media. Pressure tests on our outbound air of our existing biofilter systems 40 can be used to indicate when the media 60 may be approaching the need to be refreshed. The primary design criteria used for the size of the biofilter 40 is based on the Empty Bed Contact Time (EBCT). This calculation is the amount of time that the exhaust air is in contact with the media. In one embodiment, the minimum EBCT for removing the odors from this design is about 7 seconds. In one embodiment, the biofilter 40 for each pod will have a footprint of 294 feet long by 40 feet wide with a media depth of 3 feet. This equates to a biofilter media volume of 35,280 cubic feet. The air volume being exhausted by the exhaust fans was 204,400 cfm. If you divide the cfm's by 60 seconds equates it to 3,406 cubic feet per second. To determine the EBCT, one divides the cubic feet of media of 35,280 by the air flow of 3,406 cubic feet per second to result in an EBCT for this design of 10.35 seconds of retention time.

Recommended moisture contents for biofilters range from 40 to 65%. During warmer and dryer months, additional moisture may need to be added to maintain these levels. Generally, this addition is accomplished using sprinklers or soakers located on top of the media. This approach typically has difficulty penetrating down through the media as the exhaust air is forcing against the sprinkler water flow. With the design of the greenhouses 20 and the fact that air that has absorbed moisture from the drying process is exhausted, the ability of the media to maintain the desired moisture content is improved.

While the invention has been illustrated and described in detail in the drawings and foregoing description, the same is to be considered as illustrative and not restrictive in character, it being understood that only certain exemplary embodiments have been shown and described and that all changes and modifications that come within the spirit of the inventions are desired to be protected.

In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A system, comprising:

a. a greenhouse for predrying a biosolids to reduce volume and weight;

b. a conveyer belt operably connected to the greenhouse for conveying the biosolids from the greenhouse to a pasteurization system;

c. the pasteurization system comprising a burner-fan to introduce hot air to the biosolids;

d. the pasteurization system comprising an air permeable heat up belt to accept the biosolids from the greenhouse and a burner-fan for raising the biosolids temperature from ambient to at least 70° C.;

e. the pasteurization system further comprising an air permeable pasteurization belt that is set on a cycle time of at least thirty minutes and configured to automatically hold the biosolids at a temperature of at least 70° C. for at least thirty minutes;

f. a biofilter system operably connected with the greenhouse and the pasteurization system for reducing odors; and g. a bagging area to collect a final product.

2. The system of claim 1 wherein the greenhouse further comprises air handlers for removing moist air and introducing fresh air.

3. The system of claim 1 wherein the greenhouse further comprises exhaust fans for removing moist air and introducing fresh air.

4. The system of claim 2 wherein the biofilter system is operably connected with the air handlers to remove odors from the air.

5. The system of claim 3, wherein the biofilter system is operably connected with the exhaust fans to remove odors from the air.

6. The system of claim 1 wherein the burner-fan is fueled with natural gas, liquid petroleum, digester gas, landfill gas, methane or electricity.

7. The system of claim 1 wherein the greenhouse comprises at least two pods wherein each of the pods comprises a plurality of chambers.

8. The system of claim 1 wherein the heat up belt and pasteurization belt have a variable speed control.

9. The system of claim 1 wherein the biofilter system comprises a wood-chip/organic mulch blend.

10. The system of claim 7 wherein the biofilter system comprises a moisture content control.

11. The system of claim 1 wherein the biofilter system comprises at least one packed-tower wet scrubber.

12. The system of claim 1 wherein the biofilter system comprises at least one fine-mist wet scrubber.

13. The system of claim 1, wherein the biofilter system comprises at least one activated carbon absorber.

14. The system of claim 1 wherein the biofilter system comprises at least one thermal oxidizer.

15. The system of claim 1 wherein the biofilter system comprises an air discharge stack, wherein the air discharge stack extends at least 30 feet above the biofilter system.

16. The system of claim 1 wherein the biofilter system comprises an organic mulch based media.

17. The system of claim 1 wherein the heat up belt is configured to deliver the biosolids to the pasteurization belt after the burner-fan raises the biosolids temperature from ambient to at least 70° C.

* * * * *